United States Patent [19]

Kuwata et al.

[11] Patent Number: 4,983,388

[45] Date of Patent: Jan. 8, 1991

[54] PROCESS OF PREPARING SILICONE COMPOSITION, AND COSMETIC AND LUSTERING MATERIALS CONTAINING SILICONE COMPOSITION OBTAINED

[75] Inventors: Satoshi Kuwata, Annaka; Takahiro Goi, Kanra; Takaaki Shimizu; Tsutomu Ogihara, both of Jyouetsu, all of Japan

[73] Assignee: Shin-Etsu Chemical Co., Ltd., Tokyo, Japan

[21] Appl. No.: 405,927

[22] Filed: Sep. 11, 1989

[30] Foreign Application Priority Data

Sep. 12, 1988 [JP] Japan ................... 63-229298

[51] Int. Cl.$^5$ ............................................ A61K 31/695
[52] U.S. Cl. ...................................... 424/401; 424/63; 514/63; 514/844
[58] Field of Search ............... 424/400, 401, 63, 69; 514/63, 844, 846, 847

[56] References Cited

U.S. PATENT DOCUMENTS 3,846,550  11/1974  Akrongold et al. ................ 424/69
4,462,981   7/1984  Smith ................................. 424/401

OTHER PUBLICATIONS

Chemical Abstracts, vol. 110, 121049w (1989).

*Primary Examiner*—Thurman K. Page
*Attorney, Agent, or Firm*—Millen, White & Zelano

[57] ABSTRACT

A process for preparing a silicone composition is provided, which comprises a step of distilling away an organic solvent from a mixture of (1) a low viscosity silicone oil represented by the general formula, $R_aSiO_{(4-a)/2}$ (wherein R's may be the same or different, each being an unsubstituted or substituted, monovalent hydrocarbon residue containing 1 to 6 carbon atoms; and "a" ranges from 1.8 to 2.3), and having a viscosity of 100 centistokes or less at 25° C., with (2) an organosilica sol containing, as a dispersoid, spherical porous trimethylsilylated silica particles having an average particle size of 10 to 100 millimicrons, a specific surface area of 300 m$^2$/g or above, a trimethylsilyl group density of 0.5 to 10 micromol/m$^2$, an alkoxy group density of 0.5 to 10 micromole/m$^2$, and a silanol group density of 0.5 to 5 micromol/m$^2$, and a step of homogeneously kneading the resulting mixture under shearing stress. The thus prepared silicone composition has not only low toxicity and low stimulability but also excellent homogeneity, smoothness and extensibility, so it is well suited to be used as base ingredient of cosmetic, medical or lustering materials.

18 Claims, No Drawings

PROCESS OF PREPARING SILICONE COMPOSITION, AND COSMETIC AND LUSTERING MATERIALS CONTAINING SILICONE COMPOSITION OBTAINED

FIELD OF THE INVENTION

This invention relates to a process for preparing a silicone composition and, more particularly, to a process for preparing a paste- or grease-form silicone composition containing a low viscosity silicone oil and to products prepared therefrom as a base oil.

BACKGROUND OF THE INVENTION

Paste- or grease-form compositions containing a silicone oil as a main component have so far been used in many industrial fields.

Particularly in medical and cosmetic industries, application of low viscosity silicone oils have been widely examined in recent years. This is because low viscosity silicone oils are not only have low toxicity and low skin stimulation, but also light in extension and excellent in refreshment feeling at the time of use.

In using low viscosity silicone oils, however, it is necessary to increase a compounding amount of a thickener (a consistency increasing agent). The use of a large amount of conventional thickener, including inorganic materials such as silica fine powder, kaolin, talc, sericite, bentonite, etc., and organic materials such as lithium soap, aluminum soap, etc. (reference: *Plastic Zairyo Koza* [9] *Keiso Jushi*, page 81, Nikkan Kogyo Shinbunsha), has the defects of being responsible for the difficulty in preparing a smooth and homogeneous composition, and making the prepared composition tend to separate and to discharge the silicone oil, that is, be deficient in storage stability.

Under these circumstances, relatively high viscosity silicone oils with a viscosity of 100 centistokes or above at 25° C. have so far been used as a base oil in most cases.

However, paste- or grease-form silicone compositions using the high viscosity silicone oils described above as base oils are heavy in extension, and to make the matter worse, they leave a sticky feeling to skin after use. Therefore, cream-, stick-, ointment- and cake-form compositions utilizing such silicone compositions as described above naturally have their limitations in qualities.

On the other hand, conventional organosilica sols have generally been used as a thickener free from secondary aggregation. Those organosilica sols are usually prepared by converting colloidal silica produced from water glass into alcohol solutions through azeotropic distillation. Consequently, at the surfaces of individual silica particles are present the alkoxy groups produced by the reaction of silanol groups with the alcohol at a coverage of 1 to 3 micromol/m$^2$ and unreacted silanol groups at a high coverage of 5 to 10 micromol/m$^2$.

Therefore, these silica particles are poor in affinity for a silicone oil, and when such an organosilica sol as described above is compounded with a silicone oil, recombination reaction between silanol groups remaining unreacted at the surfaces of silica particles takes place at the time of mixing or removal of the solvent by distillation to cause aggregation of silica particles, and silica particles then separate as a precipitate from the silicone oil.

As described above, it was difficult to obtain compositions excellent in homogeneity even when a production process of compounding the conventional organosilica sol with a silicone oil was adopted.

SUMMARY OF THE INVENTION

As a result of our concentrated study for solving the above-described problems, it has now been found that remarkably favorable results can be obtained by preparing a dispersion of particular fine grain silica as a thickener, and mixing the dispersion with a base oil homogeneously under shearing stress even when a low viscosity silicone oil is used as the base oil, thus achieving this invention.

Therefore, an object of this invention is to provide a process for preparing a smooth, homogeneous, paste- or grease-form silicone composition which contains a low viscosity silicone oil as a base oil, and can give a pleasant impression when applied to skin or the like.

That is, in a process aspect this invention relates to a process for preparing a silicone composition, which comprises distilling away an organic solvent from a mixture of (1) a low viscosity silicone oil represented by the general formula, $R_a SiO_{(4-a)/2}$ (wherein the R's may be the same or different, each being an unsubstituted or substituted, monovalent hydrocarbon residue containing 1 to 6 carbon atoms; and "a" ranges from 1.8 to 2.3), and having a viscosity of 100 centistokes or less at 25° C., and (2) an organosilica sol containing, as a dispersoid, spherical porous trimethylsilylated silica particles having an average particle size of 10 to 100 millimicrons, a specific surface area of 300 m$^2$/g or more, a trimethylsilyl group density of 0.5 to 10 micromol/m$^2$, an alkoxy group density of 0.5 to 10 micromol/m$^2$, and a silanol group density of 0.5 to 5 micromol/m$^2$, and homogeneously kneading the resulting mixture under shearing stress; and in a composition aspect relates to cosmetic materials and lustering materials containing the thus prepared silicone composition.

A silicone composition prepared in accordance with this invention presents an appearance of a homogeneous, smooth, transparent or translucent paste or grease with excellent extensibility. Therefore, it is incomparably superior in characteristics to conventional, homogeneity- and extensibility- deficient, milky compositions prepared by compounding fine powdery silica with low viscosity silicone oils, and best fitted to be used in particular as cosmetic material or lustering material.

DETAILED DESCRIPTION OF THE INVENTION

R's of the low viscosity silicone oil represented by the foregoing formula $R_a SiO_{(4-a)/2}$ are unsubstituted or substituted, same or different, monovalent hydrocarbon residues containing 1 to 6 carbon atoms, with specific examples including alkyl groups such as methyl, ethyl, propyl, butyl, pentyl, hexyl, cyclohexyl, etc., phenyl group, and substituted hydrocarbon residues derived from the above-cited groups by replacing one or more of a hydrogen atom thereof by a halogen atom such as fluorine, chlorine, bromine, etc., a cyano group or so on, e.g., γ-trifluoropropyl group, chloromethyl group, and so on. Of these monovalent hydrocarbon residues, methyl and phenyl groups are particularly favored over the others. The low viscosity silicone oil may have any structure, i.e., a chain, cyclic or branched form.

The viscosity of the low viscosity silicone oil, those employable in this invention are below 100 centistokes at 25° C. This is because when a silicone oil with a viscosity of 100 centistokes or above is used as base oil, the resulting silicone composition is heavy in extension and imparts a sticky impression when applied, e.g., to skin. From these points of view, it is particularly preferred in this invention to use a silicone oil with a viscosity of 20 centistokes or less.

An organosilica sol to be used in this invention utilizes a silica sol which is prepared using an alkoxysilane as starting material and has alkoxy groups and trimethylsilyl groups at the individual particle surfaces of silica, and it is prepared by dispersing, into an organic solvent as described hereinafter, the foregoing silica sol, which comprises spherical porous silica particles having an average particle size of 10 to 100 microns and a specific surface area of 300 m$^2$/g or more. When an average size of the above-described silica particles is larger than 100 microns, the silicone composition obtained by mixing such an organosilica sol with the above-described low viscosity silicone oil is poor in homogeneity, and brings about a milky turbidity. Further, the silicone oil tends to separate out after long-term storage. Therefore, silica particles with a large average size as described above are undesirable in this invention. On the other hand, those with an average particle size smaller than 10 microns are difficult to provide an organosilica sol which can stably show its abilities.

When the above-described silica particles have a specific surface area of 300 m$^2$/g or less, they become poor in silicone oil holding power, which results in reduction of their thickening effect, and further the silicone oil tends to separate from the silicone composition during long-term storage. Therefore, they are also undesirable.

By controlling the density of silanol groups with alkoxy groups, it is possible to prevent a separation of a silicone oil from a silicone composition. Thus, with a silica sol having a silanol group density controlled to 0.5 to 5 micromol/m$^2$ with alkoxy groups is used in this invention. When the silanol group density is higher than 5 micromol/m$^2$, the recombination occurs between silanol groups at the silica surface in spite of the trimethylsililation treatment which is previously given to the silica surface, followed by separation of silica particles through aggregation. On the other hand, silanol group densities less than 0.5 micromol/m$^2$ cannot produce a satisfactory thickness-providing effect. Therefore, it is required that the silanol group density at the silica surface to range from 0.5 to 5 micromol/m$^2$.

Besides the control of the silanol group density, alkoxy groups at the surface of individual silica particles are replaced by trimethylsilyl groups in a density of 0.5 to 10 micromol/m$^2$ to hinder the recombination between silanol groups through the steric effect, whereby it becomes feasible to disperse stably the silica particles into the silicone oil. In addition, trimethylsilyl groups contribute to the dispersion stability since they can enhance wettability of the silica particles by the silicone oil.

When the density of trimethylsilyl groups is 0.5 micromol/m$^2$ or less, properties of trimethylsilyl groups, such as their steric effect, their wettability for the silicone oil and so on, are lowered, and the resulting silica particles are poor in affinity for the silicone oil. On the other when the density range beyond 10 micromol/m$^2$ exceeds the density limit for introduction of trimethylsilyl groups to the silica surface, the introduction of trimethylsilyl groups beyond that density is extremely difficult.

Any organic solvent may be used in the organosilica sol of this invention provided the low viscosity silicone oils can be dissolved therein. In general, aliphatic alcohols, e.g., ethanol, 2-propanol, etc., aromatic hydrocarbons, e.g., toluene, xylene, etc., aliphatic or alicyclic hydrocarbons, e.g., n-pentane, n-hexane, cyclohexane, etc., and halogenated hydrocarbons, e.g., dichloromethane, chloroform, carbon tetrachloride, trichloroethane, trichloroethylene, fluorochlorohydrocarbons, etc., can be used.

In this invention, the above-described low viscosity silicone oil and the organosilica sol are mixed in the desired ratio and then the mixture is heated, under reduced pressure if needed, with stirring to render the mixture homogeneous, whereby the organic solvent of the organosilica sol is distilled away. As for the mixing ratio therein, it is desired that proportions of the silicone oil and the spherical porous silica particles are 50–95 wt. % and 5–50 wt. %, respectively, to the resulting composition. More preferably, the low viscosity silicone oil is compounded with the organosilica sol so that a proportion of the low viscosity silicone oil may be 70 to 90 wt. % and that of the spherical porous silica particles may be 10 to 30 wt. %. When the low viscosity silicone oil is contained in a proportion of 95 wt. % or more (namely, the spherical porous silica particles are contained in a proportion of 5 wt. % of less), the resulting composition cannot be a paste form or a grease form, whereas when the proportion of the low viscosity silicone oil is 50 wt. % or less (namely, that of the spherical porous silica particles is 50 wt. % or more) the resulting composition is too hard to impart a good impression when put to use.

This invention doesn't have any particular limitation as to the stirring apparatus for homogeneous mixing. However, it is desirable to choose such an apparatus as to enable the efficient stirring from the central part of the container to the environs near to the container wall, because the viscosity of the mixture increases at the latter half of the procedure for the removal of the organic solvent then the mixture becomes a paste form. For instance, a planetary type stirring apparatus is well suited for this invention.

As for the shearing stress applying apparatus for the homogeneous kneading after the removal of the organic solvent, a three-rod roll mill, a two-rod roll mill, a colloid mill, a sand grinder mill, a Gaulin homogenizer, and so on can be employed. Among them, a three-rod roll mill is used to the greatest advantage. If the homogeneous kneading under shearing stress is not carried out, homogeneous dispersion of finely divided silica is incomplete, and the silicone composition obtained is poor in smoothness and tends to cause the oil separation.

Since the spherical porous silica, which is unique in its weak cohesive force in silicone oils as described above in detail, is mixed homogeneously with the low viscosity silicone oil, not only the silicone composition obtained is low intoxicity and has low stimulative effect to skin, but also when made into cream, stick, paste, ointment or cake, it can impart thereto high qualities including a good impression upon application.

Accordingly, the cosmetic materials and the medical materials containing as a base agent the silicone composition prepared in accordance with this invention have incomparable superiority to conventional materials of similar kinds. In addition, excellent extensibility of this composition is extremely effective for use as the base agent of lustering materials for cars, furniture and so on. Namely, the lustering materials utilizing this silicone composition as a base agent are advantageous in that they can impart a light impression when put to use.

EXAMPLE

This invention will now be illustrated in more detail by reference to the following examples. However, the invention should not be construed as being limited to these examples.

Additionally, in the following examples, the viscosities are values at 25° C., and the consistencies are measured according to JISK 2220.

SYNTHESIS EXAMPLE OF ORGANOSILICA SOL

In a 10-liter flask made of glass which was equipped with a stirring motor, a dropping funnel and a thermometer, were placed 182 ml of 29 wt. % aqueous ammonia, 110 ml of ion exchange water and 5542 ml of ethanol. Thereto, a solution consisting of 518 ml of tetramethoxysilane and 648 ml of ethanol was added dropwise over a period of about 1 hour with vigorously stirring while the reaction system was kept at 38° C. After the completion of the addition, the stirring was continued for 30 minutes. Then, the solution was taken out, and concentrated till the silica concentration became 10 wt. %. To the thus obtained ethanol silica sol was slowly added 145 g of trimethylchlorosilane, followed by 5 hours of stirring at room temperature. Next, 3000 ml of xylene was added to the resulting silica sol, and the ethanol was distilled away therefrom. Thereafter, the residue was neutralized by the addition of saturated sodium bicarbonate aqueous solution, the thus sedimented matter was removed by filtration, and the filtrate was concentrated to yield a silica sol dispersed in xylene with a silica content of 27 wt. % (xylene sol (1)). According to observation under an electron microscope, the silica particles dispersed in this xylene sol (1) had a spherical form. Further, the average diameter and the specific surface area of the silica particles were determined in accordance with a turbidmetric method and a BET method utilizing nitrogen adsorption, respectively. Their values were 27 millimicrons and 470 m$^2$/g, respectively. Further, the surface condition of the xylene sol (1) was examined, whereby it was revealed that silanol groups were present at a coverage of 1.0 micromol/m$^2$, ethoxy groups at a coverage of 4.9 micromol/m$^2$, and trimethylsilyl groups at a coverage of 5.1 micromol/m$^2$.

EXAMPLE 1 TO 4

In a 5-liter planetary mixer, trimethylsilyl end-blocked dimethylsilicone oil (viscosity at 25° C.: 6 centistokes) and the xylene sol (1) were compounded in such a ratio as set forth in Table-1, and heated to 70°–80° C. with stirring under reduced pressure of 5 mmHg or less to effect the stripping procedure. After the evaporation of xylene was no longer detectable, the resulting composition was allowed to stand until it cooled to room temperature, and then kneaded three times with a three-rod roll mill. Thus, the compositions as set forth in Table-1 were obtained. Each showed an appearance a transparent or translucent, homogeneous paste or grease, and a be very lightly extended over skin, and did not given any stickiness, but impart a refreshed feeling to the skin.

TABLE-1

| Example No. | | 1 | 2 | 3 | 4 |
|---|---|---|---|---|---|
| Amounts Compounded (Kg) | Dimethylsilicone Oil | 2.0 | 1.6 | 1.0 | 1.0 |
| | Xylene Sol(1) | 0.82 | 1.48 | 1.24 | 1.59 |
| Silica Content in Composition (%) | | 10 | 20 | 25 | 30 |
| Characteristics of Composition | Appearance | paste | grease | grease | grease |
| | Viscosity (CP) | 12,000 | — | — | — |
| | Unworked Penetration | — | 350 | 300 | 250 |
| | Worked Penetration | — | 360 | 300 | 260 |

EXAMPLE 5 TO 8

The compositions set forth in Table-2 were prepared in the same manner as in Examples 1 to 4, except trimethylsilyl end-blocked methylphenylsilicone oil (viscosity at 25° C.: 20 cst) was used in place of the trimethylsilyl end-block dimethylsilicone oil. Each of the thus obtained compositions had an of a translucent, homogeneous paste or grease, and, in analogy with Examples 1 to 4, it was very lightly extended over skin and did not leave a sticky feeling on the skin, but give a refreshed impression to the skin.

TABLE-2

| Example No. | | 5 | 6 | 7 | 8 |
|---|---|---|---|---|---|
| Amounts Compounded (Kg) | Methylphenylsilicone Oil | 2.0 | 1.6 | 1.0 | 1.0 |
| | Xylene Sol(1) | 0.82 | 1.48 | 1.24 | 1.59 |
| Silica Content in Composition (%) | | 10 | 20 | 25 | 30 |
| Characteristics of Composition | Appearance | paste | paste | grease | grease |
| | Viscosity (CP) | 8,800 | 120,000 | — | — |
| | Unworked Penetration | — | — | 360 | 320 |
| | Worked Penetration | — | — | 370 | 330 |

COMPARATIVE EXAMPLE 1

The xylene sol (2) was prepared in the same manner as the foregoing xylene sol (1), except that the amount of 29 wt. % aqueous ammonia, the amount of ion exchange water, the amount of ethanol and the reaction temperature in the above-described synthesis example of the organosilica sol were changed to 365 ml, 0 ml, 5469 ml and 20° C., respectively.

In the xylene sol (2), the silica content was 20 wt. %, the particle diameter was 200 millimicrons, the specific surface area was 350 m$^2$/g. According to the examination of the surface condition, silanol groups were present at a coverage of 0.7 micromol/m$^2$, ethoxy groups at a coverage of 4.8 micromol/m$^2$, and trimethylsilyl groups at a coverage of 5.0 micromol/m$^2$. The silicone composition was prepared in the same manner as the foregoing examples 1 to 4, except 0.7 Kg of trimethylsilyl end-blocked dimethylsilicone (viscosity at 25° C.: 6 cst) and 1.5 Kg of the xylene sol (2), in place of the before mentioned xylene sol (1), were compounded. The resulting composition, though had a silica content of 30 wt. % similarly to the example 4, was a milky liquid with a viscosity of 460 CP. In addition, oil caused this composition to become heterogeneous after 24 hours' standing.

COMPARATIVE EXAMPLE 2 TO 4

In a 5-liter planetary mixer, trimethylsilyl end-blocked dimethylsilicone oil (viscosity at 25° C.: 6 cst) and trimethylsilyl-processed amorphous silica (average particle size: 20 millimicrons, specific surface area: 130 m$^2$/g, trimethylsilyl content: 6.7 micromol/g) were compounded, and stirred for one hour at room temperature. The composition obtained was kneaded three times with a three-rod roll mill. Thus, each of the compositions set forth in Table-3 was prepared. All of these compositions, though translucent and homogeneous, were viscous and heavy in extension over skin, and further gave a sticky feeling.

TABLE-3

| Comparative Example No. | | 2 | 3 | 4 |
| --- | --- | --- | --- | --- |
| Amounts Compounded (Kg) | Dimethylsilicone Oil | 1.8 | 1.6 | 1.4 |
| | Trimethlsilyl-Processed Silica Fine Powder | 0.20 | 0.40 | 0.60 |
| Characteristics of Composition | Appearance | paste | grease | grease |
| | Viscosity (CP) | 5,800 | — | — |
| | Unworked Penetration | — | 350 | 230 |
| | Worked Penetration | — | 420 | 310 |

What is claimed is:

1. A process for preparing a silicone composition, which comprises distilling away an organic solvent from a mixture of (1) a low viscosity silicone oil represented by the general formula, $R_a SiO_{(4-a)/2}$ wherein the R's may be the same or different, each being an unsubstituted or substituted, monovalent hydrocarbon residue containing 1 to 6 carbon atoms; and "a" ranges from 1.8 to 2.3, and having a viscosity of 100 centistokes or less at 25° C., and (2) an organosilica sol containing, as a dispersoid, spherical porous trimethylsilylated silica particles having an average particle size of 10 to 100 millimicrons, a specific surface area of 300 m$^2$/g or above, a trimethylsilyl group density of 0.5 to 10 micromol/m$^2$, and alkoxy group density of 0.5 to 10 micromol/m$^2$, and a silanol group density of 0.5 to 5 micromol/m$^2$, and homogeneously kneading the resulting mixture under shearing stress.

2. The process for preparing a silicone composition as described in claim 1, wherein a compounding fraction of said low viscosity silicone oil from 95 to 50 wt. %, and of said spherical porous silica particles from 5 to 50 wt. % is employed.

3. The process for preparing a silicone composition as described in claim 1, wherein R in the general formula, $R_a SiO_{(4-a)/2}$, methyl group a phenyl group.

4. The process for preparing a silicone composition as described in claim 1, wherein said low viscosity silicone oil has a viscosity of 20 centistokes or less.

5. The process for preparing a silicone composition as described in claim 1, wherein an organic solvent in which said low viscosity silicone oil is soluble is used as the solvent for said organosilica sol.

6. The process for preparing a silicone composition as described in claim 1, wherein the removal of an organic solvent from said organosilica sol is performed with a planetary stirring apparatus.

7. The process for preparing a silicone composition as described in claim 1, wherein the homogeneous kneading under shearing stress is carried out with a three-rod roll mill.

8. A silicone composition in the form of a homogeneous, smooth, transparent or translucent paste or grease, consisting essentially of a stable homogeneous dispersion of 50–95 wt. % of spherical porous trimethylsilylated silica particles having an average particle size of 10 to 100 microns and a specific surface area of at least 300 m$^2$/g, a trimethylsilyl group density of 0.5 to 10 micromol/m$^2$, and alkoxy group density of 0.5 to 10 micromol/m$^2$, and a silanol group density of 0.5 to 5 micromol/m$^2$, in a low viscosity silicone oil represented by the general formula $R_a SiO_{(4-a)/2}$, wherein the R's may be the same or different, each being an unsubstituted or substituted, monovalent hydrocarbon residue containing 1 to 6 carbon atoms; and "a" ranges from 1.8 to 2.3, and having a viscosity of 100 centistokes or less at 25° C.

9. The process of claim 1, wherein the silicone oil has a viscosity of 20 centistokes or less.

10. The process of claim 1, wherein the silicone oil is a trimethylsilyl end-blocked dimethylsilicone or methylphenyl silicone oil.

11. The process of claim 1, wherein a ratio of the silicone oil to the silica particles of from 70 to 90 wt. % to 30 to 10 wt. %, respectively, is employed.

12. The process of claim 11, wherein the silicone oil has a viscosity of 20 centistokes or less and wherein the silicone oil is a trimethylsilyl end-blocked dimethylsilicone or methylphenyl silicone oil.

13. A cosmetic material containing a silicone composition of claim 8.

14. A silicone composition according to claim 8, wherein R is one or both of methyl and phenyl.

15. A silicone composition according to claim 8, wherein the silicone oil has a viscosity of 20 centistokes or less.

16. A silicone composition according to claim 8, wherein the silicone oil is a trimethylsilyl end-blocked dimethylsilicone or methylphenyl silicone oil.

17. A silicone composition according to claim 8, wherein the ratio of the silicone oil to the silicone particles is 70 to 90 wt. % to 30 to 10 wt. %, respectively.

18. A silicone composition according to claim 17, wherein the silicone oil has a viscosity of 20 centistokes or less and wherein the silicone oil is a trimethylsilyl end-blocked dimethylsilicone or methylphenyl silicone oil.

* * * * *